US006018051A

United States Patent [19]

Tanimoto et al.

[11] Patent Number: 6,018,051

[45] **Date of Patent: *Jan. 25, 2000**

[54] PROCESSING FOR WASHING-OUT DEGRADATION-RESISTANT ORGANIC CHLORINE COMPOUND

[75] Inventors: Fumio Tanimoto, Kyoto; Tsuneo Yano, Hanno, both of Japan

[73] Assignees: Research Institute for Production Development, Kyoto; Mitsui & Co., Ltd., Tokyo; NEOS Co., Ltd., Kobe, all of Japan

[ * ] Notice: This patent is subject to a terminal disclaimer.

[21] Appl. No.: 09/091,027

[22] PCT Filed: Oct. 2, 1997

[86] PCT No.: PCT/JP97/03573

§ 371 Date: Sep. 8, 1998

§ 102(e) Date: Sep. 8, 1998

[87] PCT Pub. No.: WO98/15361

PCT Pub. Date: Apr. 16, 1998

[30] Foreign Application Priority Data

Oct. 9, 1996 [JP] Japan .................................... 8-287448

[51] Int. Cl.[7] ....................... C07D 233/28; C07D 233/30

[52] U.S. Cl. .................................... 548/316.4; 548/326.1; 570/204; 570/190; 474/116.1; 474/116.4; 474/181

[58] Field of Search ............................. 548/316.4, 326.1; 474/116.1, 116.4, 181; 570/204, 190

[56] References Cited

U.S. PATENT DOCUMENTS

| | | |
|---|---|---|
| 4,447,541 | 5/1984 | Peterson . |
| 4,853,040 | 8/1989 | Mazur et al. . |
| 5,648,499 | 7/1997 | Tanimoto et al. .................. 548/316.5 |

OTHER PUBLICATIONS

Patent Abstracts of Japan, publication No. 07289656A, dated Nov. 7, 1995.

Patent Abstracts of Japan, publication No. 07313620A, dated Dec. 5, 1995.

*Primary Examiner*—James O. Wilson
*Assistant Examiner*—Howard Owens
*Attorney, Agent, or Firm*—Rosenthal & Osha L.L.P.

[57] ABSTRACT

In order to subject a cellulosic material such as insulating paper onto and into which transformer high-voltage insulating oil containing PCB has adhered and permeated to washing that removes the PCB etc. to an undetectable value, the cellulosic material to which PCB etc. has adhered is placed in DMI, sulfolane or other aprotic solvent containing an alkali such as caustic soda and stirred.

1 Claim, No Drawings

PROCESSING FOR WASHING-OUT DEGRADATION-RESISTANT ORGANIC CHLORINE COMPOUND

TECHNICAL FIELD

This invention relates to a chemical treatment process for safely washing a degradation-resistant organic chlorine compound out of a cellulose-containing material having the degradation-resistant organic chlorine compound adhered thereto.

BACKGROUND ART

Pressure-sensitive papers with adhered polychlorobiphenyl (PCB) and other degradation-resistant organic chlorine compounds (hereinafter PCB etc.) remain in storage for the lack of a safe process for treating the pressure-sensitive paper. On the other hand, methods for draining transformers, oil capacitors and other electrical equipment of PCB etc. and then washing them with a solvent such n-hexane are being promoted. However, removal of PCB etc. adhering to the paper, wood and the like incorporated in such electrical equipment and the like is extremely difficult and no safe treatment process for this purpose has yet been discovered.

Since n-hexane and other such solvents have low viscosity and are excellent solvents of PCB etc., the ordinary washing operation is highly effective for washing metals, plastics and the like, only requiring that care be taken regarding the low solvent ignition point. PCB etc. remaining after recovery of n-hexane or the like from the washing solution can therefore be safely and completely broken down by the method under the inventors' earlier application (Japanese Patent Public Disclosure Hei 7-8572). However, a treatment process using n-hexane or the like cannot completely extract and break down PCB etc. adhering to paper, wood or other such materials containing cellulose.

The object of this invention is therefore to provide a washing and removal process which completely extracts and breaks down PCB etc. from a cellulose-containing material having adhered PCB etc.

DISCLOSURE OF THE INVENTION

Having discovered through many years of research into chemical extraction and decomposition of PCB etc. that this can be completely achieved by using a strong alkali in a special aprotic solvent, the inventors filed several patent applications (Japanese Patent Public Disclosure Nos. 7-289656 and 7-313620). They also ascertained that these inventions exhibit a dramatic effect in efficiently washing PCB etc. out of a cellulose-containing material having adhered PCB etc., whereby they accomplished this invention.

Specifically, the process for washing out PCB etc. according to this invention is characterized in bringing a cellulose-containing material having the PCB etc. adhered thereto into contact with a strong alkali in a solution containing not less than 50% of one of 1,3-dimethyl-2-imidazolidinone (hereinafter DMI) and sulfolane or a mixture of these two aprotic solvents.

The inventors learned through a long series of experiments that PCB etc. are dramatically removed when a cellulose-containing material having adhered PCB etc. is contacted with a strong alkali in an alkali-resistant, high-boiling-point solvent containing not less than 50% of one of DMI and sulfolane or a mixture of these two solvents.

With regard to this invention, "PCB etc." refers to, for example, polychlorobiphenyl (hereinafter PCB), polychlorodioxin, polychloroterphenyl, polychloronaphthalene, polychlorobenzene derivative, and mixtures of these. With regard to this invention, "cellulose-containing material having adhered PCB etc." refers mainly to, for example, paper, formed articles of copper and aluminum such as wire, thin sheet and the like used in transformer coils and other such electrical equipment, and bamboo and other woods used as support materials in such electrical equipment. The cellulose-containing material having adhered PCB etc. may also of course be cotton cloth or linen cloth contaminated by adherence of PCB etc. The term cellulose-containing material having adhered PCB etc. also encompasses pressure-sensitive paper, such as business forms, made of paper coated with microcapsules containing a mixture of PCB etc. and coloring dye.

With regard to this invention, "alkali" refers to caustic soda, caustic potash, sodium alcoholate, potassium alcoholate, calcium hydroxide, calcium oxide, aluminum hydroxide, aluminum oxide, sodium carbonate, potassium carbonate, calcium carbonate, alkylamine, alkanolamineurea, alkyleneurea, quinoline and the like. Particularly preferable are strong alkalis such as caustic soda, caustic potash, sodium alcoholate, potassium alcoholate and the like. In some cases, therefore, the invention uses caustic soda, caustic potash, sodium alcoholate, potassium alcoholate or a mixture of these strong alkali alone as the aforesaid alkali. In other cases, it uses these strong alkalis together with calcium hydroxide, calcium oxide, aluminum hydroxide, aluminum oxide, sodium carbonate, potassium carbonate, calcium carbonate, alkylamine, alkanolamineurea, alkyleneurea, quinoline or a mixture of these alkalis.

In the invention, the cellulose-containing material having adhered PCB etc. can be brought into contact with the strong alkali by finely fragmenting the cellulose-containing material having adhered PCB etc., placing it in a container, thereafter adding to the, container a mixture obtained by adding 0.5% to 10% strong alkali to a solvent containing not less than 50% of an aprotic solvent, and then mechanically mixing the contents of the container.

The treatment temperature in this case is one within the range of room temperature to 200° C. selected as an appropriate temperature condition for the purpose. To heighten the activation of the alkali, it is effective to add not only the aprotic solvent but also not more than 50% of a dioxane, poly (ethylene glycol) and/or poly (ethylene glycol) dialkylether. However, the purpose can in essence be achieved irrespective of whether or not these solvents are added.

In the dyeing and resin finishing of cellulose, a pretreatment technique is effected for mercerization by a strong alkali aqueous solution. It was discovered that in the present nonaqueous method, too, the mixed system of aprotic solvent and strong alkali strongly acts on the cellulose to thoroughly remove PCB etc. Results of analysis confirm that the nature of the material is changed by loosening of the cellulose hydrogen bonds and that the adhering PCB etc. are extracted and broken down.

In contrast, n-hexane washing thoroughly removes PCB etc. adhering to metallic and other inactive surfaces but the n-hexane has no affinity for cellulose and is totally incapable of dissolving alkali. Because of this, n-hexane washing cannot remove PCB etc. from cellulose materials, which have complex surfaces and include functional groups with affinity for PCB etc.

To realize the effect of the invention, the material consisting mainly of cellulose having adhered PCB etc. must be finely fragmented by a method such as cutting or pulverizing, placed in a container for extraction and decomposition, elevated in temperature, and mixed. Although the ultrasonic washing now widely used in industry can be applied for the mixing, the ordinary mechanical mixing method unexpectedly gives better results in shorter time. That further improved results can be obtained by combining the two methods is self evident.

Although information sufficient for defining the chemical role of the aprotic solvent has not yet been secured, the aprotic solvent is thought to act on the PCB etc. As in a referential example set out later, for instance, it was ascertained that when ultrasonic stirring was effected for 0.25 hr in DMI without addition of caustic soda, PCB content fell from 6×10$^8$ ppb to 3×10$^4$ ppb even at 15° C.

BEST MODE FOR CARRYING OUT THE INVENTION

The invention will now be explained in detail with reference to examples and referential examples.

The washing conditions (solvent, alkali, temperature and reaction time) and the results (concentration of PCB content) in first to tenth examples of the invention are shown in Table 1.

EXAMPLES 2–10

In Examples 2–10, washing and removal was effected by the method of the invention in a manner similar to that of Example 1 but with the type of solvent, type of alkali, temperature, reaction time and other washing and removal conditions altered variously, as shown along with the test results in Table 1.

As indicated in Table 1, in Examples 2, 6, 7, 8, 9 and 10, as in Example 1, the treatment was effected on finely fragmented insulating paper onto and into which TFO with a PCB content of 40 ppm had adhered and permeated. In Examples 3, 4 and 5, the treatment was respectively effected on wood from inside a transformer, transformer copper wire with adhering paper, onto and into both of which TFO with a PCB content of 20 ppm had adhered and permeated, and pressure-sensitive paper. It was ascertained that all of these treatment samples could be washed and removed of PCB etc. to below the detection limit of the GC-MS by bringing them into contact with alkali in an aprotic solvent containing DMI or sulfolane.

TABLE 1

| Exmp. | Washed sample | Washing method | Solvent | Alkali (in DMI) | Temp. (° C.) | Reaction time | Total PCB (ppb) |
|---|---|---|---|---|---|---|---|
| 1 | Transformer insulating paper (w/adhered TFO containing 40 ppm PCB) | Washing w/stirring | DMI | NaOH 5% | 200 | 0 hr (raw) | 2,400 |
| | | | | | | 0.5 hr | 6.3 |
| | | | | | | 2 hr | N.D. |
| 2 | Transformer insulating paper (w/adhered TFO containing 40 ppm PCB) | Washing w/stirring | DMI | NaOH 2% | 200 | 0 hr (raw) | 2,100 |
| | | | | | | 0.5 hr | N.D. |
| | | | | | | 1 hr | N.D. |
| | | | | | | 2 hr | N.D. |
| 3 | Wood piece from inside transformer (w/adhered TFO containing 20 ppm PCB) | Washing w/stirring | DMI | NaOH 5% | 200 | 0 hr (raw) | 6,700 |
| | | | | | | 0.5 hr | 24 |
| | | | | | | 1 hr | N.D. |
| | | | | | | 2 hr | N.D. |
| 4 | Transformer copper wire (w/ adhered paper) | Washing w/stirring | DMI | NaOH 5% | 200 | 0 hr (raw) | 390 |
| | | | | | | 1 hr | N.D. |
| | | | | | | 2 hr | N.D. |
| 5 | Pressure-sensitive paper | Washing w/stirring | DMI | NaOH 5% | 200 | 0 hr (raw) | 30,000,000 |
| | | | | | | 1 hr | N.D. |
| | | | | | | 2 hr | N.D. |
| 6 | Transformer insulating paper (w/adhered TFO containing 40 ppm PCB) | Washing w/stirring | Sulfolane | KOH 2% | 200 | 0 hr (raw) | 2,100 |
| | | | | | | 1 hr | N.D. |
| | | | | | | 2 hr | N.D. |
| 7 | Transformer insulating paper (w/adhered TFO containing 40 ppm PCB) | Washing w/stirring | Sulfolane 70% Poly(ethylene glycol) 30% | KOH 2% | 200 | 0 hr (raw) | 2,100 |
| | | | | | | 1 hr | N.D. |
| | | | | | | 2 hr | N.D. |
| 8 | Transformer insulating paper (w/adhered TFO containing 40 ppm PCB) | Washing w/stirring | DMI | NaOh 1% $C_2H_5ONa$ 1% | 180 | 0 hr (raw) | 2,100 |
| | | | | | | 0.5 hr | N.D. |
| | | | | | | 1 hr | N.D. |
| | | | | | | 2 hr | N.D. |
| 9 | Transformer insulating paper (w/adhered TFO containing 40 ppm PCB) | Washing w/stirring | DNI | $C_2H_5ONa$ 2% | 160 | 0 hr (raw) | 2,100 |
| | | | | | | 0.5 hr | N.D. |
| | | | | | | 1 hr | N.D. |
| | | | | | | 2 hr | N.D. |
| 10 | Transformer insulating paper (w/adhered TFO containing 40 ppm PCB) | Washing w/stirring | Sulfolane | $C_2H_5ONa$ 2% | 180 | 0 hr (raw) | 2,100 |
| | | | | | | 0.5 hr | 24 |
| | | | | | | 1 hr | N.D. |
| | | | | | | 2 hr | N.D. |

EXAMPLE 1

Insulating paper (finely fragmented) onto and into which transformer high-voltage insulating oil (hereinafter TFO) with a PCB content of 40 ppm had adhered and permeated was cast into DMI containing 5% caustic soda and stirred with a stirring rod at 200° C. The mixture thickened after 0.5 hr and assumed a totally slurry-like consistency after 1 hr. Small amounts were sampled for measurement of PCB content concentration using a gas chromatograph-mass spectroscope (hereinafter GC-MS). The concentration was 2,100 ppb in the raw state and 6.3 ppb after 0.5 hr. After 1 hr the concentration was below the detection limit of the GC-MS (below 0.5 ppb: N.D. for short). This example thus evinces the extremely effective wash-out and removal of PCB from insulating paper to N.D. in 1 hr.

Referential Examples 1–5

Table 2 shows referential examples relative to the invention indicating cases in which washing was effected by the ultrasonic method, in which no NaOH was present during stirring and washing, and in which the treatment was effected on transformer copper wire or iron core. Referential Examples 1–4 are examples in which alkali was not added. In these examples, PCB etc. could not be completely washed out to below the detection limit of the GC-MS. In Referential Example 5, the treatment was effected on transformer iron core. It was ascertained that even when such a material was treated, the contact with the alkali in the DMI enabled wash-out of PCB etc. to below the detection limit of the GS-MS.

TABLE 2

| Ref. Exmp. | Washed sample | Washing method | Solvent | Alkali (in DMI) | Temp. (° C.) | Reaction time | Total PCB (ppb) |
|---|---|---|---|---|---|---|---|
| 1 | Transformer insulating paper (w/adhered TFO containing 40 ppm PCB) | Washing w/stirring | DMI | W/O NaOH | 200 | 0 hr (raw) | 2,100 |
| | | | | | | 0.5 hr | 1,000 |
| | | | | | | 1 hr | 500 |
| | | | | | | 2 hr | 50 |
| 2 | Transformer copper wire | Washing w/stirring | DMI | W/O NaOH | 200 | 0 hr (raw) | 390 |
| | | | | | | 1 hr | 300 |
| 3 | Transformer insulating paper (w/adhered TFO containing 40 ppm PCB) | Washing w/ultra-sonic stirring 45 KHz | DMI | W/O NaOH | 15 | 0 hr (raw) | 2,100 |
| | | | | | | 0.5 hr | 1,900 |
| | | | | | | 1 hr | 1,800 |
| | | | | | | 2 hr | 1,600 |
| 4 | Transformer insulating paper (soaked in 70% PCB) | Washing w/ultra-sonic stirring 45 KHz | DMI | W/O NaOH | 15 | 0 hr (raw) | 600,000,000 |
| | | | | | | 0.25 hr | 30,000 |
| 5 | Transformer iron core | Washing w/stirring | DMI | NaOH 2% | 200 | 0 hr (raw) | 870 |
| | | | | | | 0.5 hr | 50 |
| | | | | | | 1 hr | N.D. |
| | | | | | | 2 hr | N.D. |

Industrial Applicability

As explained in the foregoing, this invention completely washes PCB etc. out of a cellulose-containing material having adhered PCB etc. by bringing it into contact with a strong alkali in a solvent containing DMI or sulfolane. Since implementation of the invention can therefore economically and very safely contribute to environmental improvement, its industrial applicability is extremely great.

We claim:

1. A process for washing out a degradation-resistant chlorine compound at temperatures between room temperature and 200° C., comprising bringing a cellulose-containing material having the degradation-resistant chlorine adhered thereto into contact with a strong alkali in a solution containing not less than 50% of one of 1,3 dimethyl-2-imidazolidinone and sulfolane or a mixture of the two.

* * * * *